(12) United States Patent
Charlebois et al.

(10) Patent No.: US 8,985,430 B2
(45) Date of Patent: Mar. 24, 2015

(54) METHOD FOR ATTACHING A POROUS METAL LAYER TO A METAL SUBSTRATE

(75) Inventors: Steven J. Charlebois, West Lafayette, IN (US); Leslie N. Gilbertson, Warsaw, IN (US); Michael E. Hawkins, Columbia City, IN (US); Dana J. Medlin, Warsaw, IN (US); H. Ravindranath Shetty, Warsaw, IN (US); Steven A. Zawadzki, Leesburg, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 13/461,341

(22) Filed: May 1, 2012

(65) Prior Publication Data

US 2012/0234461 A1     Sep. 20, 2012

Related U.S. Application Data

(60) Division of application No. 13/027,697, filed on Feb. 15, 2011, now Pat. No. 8,191,760, which is a
(Continued)

(51) Int. Cl.
*B32B 37/12* (2006.01)
*B23P 23/00* (2006.01)
(Continued)

(52) U.S. Cl.
CPC ............ *B23P 23/00* (2013.01); *A61F 2/30767* (2013.01); *A61F 2/30907* (2013.01); *A61L 27/04* (2013.01);
(Continued)

(58) Field of Classification Search
CPC . A61F 2/30767; A61F 2/3094; A61F 2/3859; A61F 2002/30787; A61F 2002/30967; A61F 2002/30968; A61F 2002/30978; A61F 2002/3401; A61F 2310/00023; A61F 2310/00029; A61F 2310/00407; B23P 23/00

USPC .......... 228/248.1, 193, 253, 262.3, 262.31, 228/262.71, 245; 156/73.1, 242, 306.6, 156/289, 228, 581, 583.1, 156, 125; 623/23.53, 16.11, 23.36

See application file for complete search history.

(56) References Cited

U.S. PATENT DOCUMENTS 2,945,295 A   7/1960  Feaster
3,353,259 A   11/1967 Kirkpatrick
(Continued)

FOREIGN PATENT DOCUMENTS

CA     2431736         8/2012
EP     0298450    *    5/1994    ............ A61L 27/00
(Continued)

OTHER PUBLICATIONS

The Office Action mailed Nov. 14, 2006 in related European Application No. 03253855.5.
(Continued)

*Primary Examiner* — Scott Kastler
*Assistant Examiner* — Michael Aboagye
(74) *Attorney, Agent, or Firm* — Schwegman Lundberg & Woessner, P.A.

(57) ABSTRACT

A method for attaching a porous metal layer to a dense metal substrate, wherein the method is particularly useful in forming orthopedic implants such as femoral knee components, femoral hip components, and/or acetabular cups. The method, in one embodiment thereof, comprises providing a solid metal substrate; providing a porous metal structure; contouring a surface of the porous metal structure; placing the porous structure against the substrate such that the contoured surface of the porous metal structure is disposed against the substrate, thereby forming an assembly; applying heat and pressure to the assembly in conjunction with thermal expansion of the substrate in order to metallurgically bond the porous structure and the substrate; and removing mass from the substrate after the porous structure is bonded to the substrate, thereby finish processing the assembly.

16 Claims, 10 Drawing Sheets

Related U.S. Application Data continuation of application No. 11/109,166, filed on Apr. 18, 2005, now Pat. No. 7,918,382, which is a continuation-in-part of application No. 10/455,846, filed on Jun. 6, 2003, now Pat. No. 6,945,448.

(60) Provisional application No. 60/389,615, filed on Jun. 18, 2002.

(51) Int. Cl.

| | | |
|---|---|---|
| *A61F 2/30* | (2006.01) | |
| *A61L 27/04* | (2006.01) | |
| *A61L 27/30* | (2006.01) | |
| *A61L 27/56* | (2006.01) | |
| *B22F 7/00* | (2006.01) | |
| *B22F 7/06* | (2006.01) | |
| *C23C 26/00* | (2006.01) | |
| *A61F 2/38* | (2006.01) | |
| *A61F 2/34* | (2006.01) | |

(52) U.S. Cl.
CPC ............... *A61L 27/30* (2013.01); *A61L 27/56* (2013.01); *B22F 7/004* (2013.01); *B22F 7/064* (2013.01); *C23C 26/00* (2013.01); *A61F 2/3094* (2013.01); *A61F 2/3859* (2013.01); *A61F 2002/30787* (2013.01); *A61F 2002/30967* (2013.01); *A61F 2002/30968* (2013.01); *A61F 2002/30978* (2013.01); *A61F 2002/3401* (2013.01); *A61F 2310/00023* (2013.01); *A61F 2310/00029* (2013.01); *A61F 2310/00407* (2013.01); *A61F 2310/00544* (2013.01)
USPC ....................................... 228/248.1; 156/242

(56) References Cited

U.S. PATENT DOCUMENTS

| | | | |
|---|---|---|---|
| 3,605,123 | A | 9/1971 | Hahn |
| 3,852,045 | A | 12/1974 | Wheeler et al. |
| 3,855,638 | A | 12/1974 | Pilliar |
| 3,906,550 | A | 9/1975 | Rostoker et al. |
| 4,479,271 | A | 10/1984 | Bolesky et al. |
| 4,487,808 | A | 12/1984 | Lambert |
| 4,570,271 | A | 2/1986 | Sump |
| 4,612,160 | A | 9/1986 | Donlevy et al. |
| 4,636,219 | A | 1/1987 | Pratt et al. |
| 4,644,942 | A | 2/1987 | Sump |
| 4,690,320 | A | 9/1987 | Morishita et al. |
| 4,715,860 | A | 12/1987 | Amstutz et al. |
| 4,759,957 | A | 7/1988 | Eaton et al. |
| 4,851,267 | A | 7/1989 | Miyauchi et al. |
| 4,854,496 | A | 8/1989 | Bugle |
| 4,969,907 | A | 11/1990 | Koch et al. |
| 5,013,324 | A | 5/1991 | Zolman et al. |
| 5,027,998 | A | 7/1991 | Bugle |
| 5,080,672 | A | 1/1992 | Bellis |
| 5,104,410 | A | 4/1992 | Chowdhary |
| 5,192,324 | A | 3/1993 | Kenna |
| 5,198,308 | A | 3/1993 | Shetty et al. |
| 5,201,766 | A | 4/1993 | Georgette |
| 5,236,457 | A * | 8/1993 | Devanathan .................. 128/898 |
| 5,282,861 | A | 2/1994 | Kaplan |
| 5,308,412 | A | 5/1994 | Shetty et al. |
| 5,323,954 | A | 6/1994 | Shetty et al. |
| 5,326,376 | A | 7/1994 | Warner et al. |
| 5,342,659 | A | 8/1994 | Horowitz et al. |
| 5,358,527 | A | 10/1994 | Forte |
| 5,363,554 | A | 11/1994 | Partridge et al. |
| 5,387,243 | A * | 2/1995 | Devanathan .................. 128/898 |
| 5,409,703 | A | 4/1995 | McAnalley et al. |
| 5,441,537 | A | 8/1995 | Kenna |
| 5,443,510 | A | 8/1995 | Shetty |
| 5,464,440 | A | 11/1995 | Johansson |
| 5,504,300 | A | 4/1996 | Devanathan et al. |
| 5,509,899 | A | 4/1996 | Fan et al. |
| 5,571,187 | A | 11/1996 | Devanathan |
| 5,612,052 | A | 3/1997 | Shalaby |
| 5,672,284 | A | 9/1997 | Devanathan et al. |
| 5,714,159 | A | 2/1998 | Shalaby |
| 5,734,959 | A | 3/1998 | Krebs et al. |
| 5,773,789 | A | 6/1998 | Devanathan et al. |
| 5,800,552 | A | 9/1998 | Forte |
| 5,926,685 | A | 7/1999 | Krebs et al. |
| 5,973,222 | A | 10/1999 | Devanathan et al. |
| 6,049,054 | A | 4/2000 | Panchison et al. |
| 6,059,817 | A | 5/2000 | Bonutti |
| 6,063,442 | A | 5/2000 | Cohen et al. |
| 6,071,389 | A | 6/2000 | Zhang |
| 6,080,488 | A | 6/2000 | Hostettler et al. |
| 6,100,327 | A | 8/2000 | Scheckenbach |
| 6,110,483 | A | 8/2000 | Whitbourne et al. |
| 6,132,674 | A | 10/2000 | Compton et al. |
| 6,176,849 | B1 | 1/2001 | Yang et al. |
| 6,203,565 | B1 | 3/2001 | Bonutti |
| 6,410,044 | B1 | 6/2002 | Chudzik et al. |
| 6,413,539 | B1 | 7/2002 | Shalabu |
| 6,470,568 | B2 | 10/2002 | Fried et al. |
| 6,527,938 | B2 | 3/2003 | Bales et al. |
| 6,544,472 | B1 | 4/2003 | Compton |
| 6,605,293 | B1 | 8/2003 | Giordano et al. |
| 6,708,869 | B2 | 3/2004 | Hyogo et al. |
| 6,740,186 | B2 * | 5/2004 | Hawkins et al. ............... 156/242 |
| 6,945,448 | B2 * | 9/2005 | Medlin et al. ............... 228/248.1 |
| 7,077,867 | B1 | 7/2006 | Pope et al. |
| 7,686,203 | B2 | 3/2010 | Rauguth et al. |
| 7,918,382 | B2 * | 4/2011 | Charlebois et al. ......... 228/248.1 |
| 8,191,760 | B2 * | 6/2012 | Charlebois et al. ......... 228/248.1 |
| 2002/0114080 | A1 * | 8/2002 | Guest ............................ 359/620 |
| 2003/0036794 | A1 | 2/2003 | Ragheb et al. |
| 2003/0104190 | A1 | 6/2003 | Zhou |
| 2005/0090905 | A1 | 4/2005 | Hawkins |
| 2005/0112397 | A1 | 5/2005 | Rolfe et al. |
| 2005/0184134 | A1 | 8/2005 | Charlebois et al. |
| 2005/0242162 | A1 | 11/2005 | Medlin et al. |
| 2006/0073356 | A1 | 4/2006 | Justin et al. |
| 2008/0195222 | A1 | 8/2008 | Rauguth et al. |
| 2011/0132974 | A1 | 6/2011 | Charlebois et al. |
| 2013/0219685 | A1 | 8/2013 | Charlebois et al. |

FOREIGN PATENT DOCUMENTS

| | | |
|---|---|---|
| EP | 0598450A1 A1 | 5/1994 |
| EP | 1433443A1 A1 | 6/2004 |
| EP | 1398045 B1 | 6/2012 |
| GB | 2142544 A | 1/1985 |
| JP | 55-045505 A | 3/1980 |
| JP | 6-039564 A | 2/1994 |
| JP | 11-286704 A | 10/1999 |
| JP | 2003-053523 A | 2/2003 |

OTHER PUBLICATIONS

The Office Action mailed Feb. 11, 2009 in related Australian Application No. 2003204797.
The Office Action mailed May 28, 2004 in related European Application No. 03253855.5.
The Office Action mailed Jul. 8, 2008 in related European Application No. 03253855.5.
The Response filed Jan. 9, 2009 to the Office Action mailed Jul. 8, 2008 in related European Application No. 03253855.5.
The Response filed Oct. 7, 2004 to the Office Action mailed May 28, 2004 in related European Application No. 03253855.5.
The Response filed Apr. 4, 2007 to the Office Action mailed Nov. 14, 2006 in related European Application No. 03253855.5.
The Response filed Jul. 22, 2009 to the Office Action mailed Feb. 11, 2009 in related Australian Application No. 2003204797.
Office Action mailed Sep. 10, 2004 in priority U.S. Appl. No. 10/455,846.
Amendment filed Nov. 1, 2004 in priority U.S. Appl. No. 10/455,846.
Office Action mailed Mar. 3, 2005 in priority U.S. Appl. No. 10/455,846.

(56) References Cited

OTHER PUBLICATIONS

Amendment filed Mar. 21, 2005 in priority U.S. Appl. No. 10/455,846.
Office Action mailed Apr. 29, 2008 in priority U.S. Appl. No. 11/109,166.
Amendment filed Aug. 29, 2008 in priority U.S. Appl. No. 11/109,166.
Office Action mailed Mar. 6, 2009 in priority U.S. Appl. No. 11/109,166.
Amendment filed Aug. 6, 2009 in priority U.S. Appl. No. 11/109,166.
Office Action mailed Dec. 3, 2009 in priority U.S. Appl. No. 11/109,166.
Amendment filed Apr. 5, 2010 in priority U.S. Appl. No. 11/109,166.
Office Action mailed May 27, 2010 in priority U.S. Appl. No. 11/109,166.
Amendment filed Sep. 24, 2010 in priority U.S. Appl. No. 11/109,166.
312 Amendment filed Dec. 22, 2010 in priority U.S. Appl. No. 11/109,166.
312 Amendment filed Dec. 30, 2010 in priority U.S. Appl. No. 11/109,166.
Zimmer Technical Memorandum, 1287.02, The Sintering cycle for the Trabecular Metal Acetabular cups, May 30, 2002.
U.S. Appl. No. 10/455,846, Notice of Allowance mailed May 10, 2005, 8 pgs.
U.S. Appl. No. 11/109,166, Notice of Allowance mailed Dec. 9, 2010, 10 pgs.
U.S. Appl. No. 11/109,166, PTO Response to 312 Amendment mailed Jan. 4, 2011, 2 pgs.
U.S. Appl. No. 11/146,571, Appeal Brief filed May 2, 2011, 37 pgs.
U.S. Appl. No. 11/146,571, Examiner Interview Summary mailed Sep. 3, 2009, 4 pgs.
U.S. Appl. No. 11/146,571, Examiner's Answer to Appeal Brief mailed Jul. 11, 2011, 20 pgs.
U.S. Appl. No. 11/146,571, Final Office Action mailed Oct. 14, 2008, 10 pgs.
U.S. Appl. No. 11/146,571, Final Office Action mailed Nov. 24, 2009, 17 pgs.
U.S. Appl. No. 11/146,571, Final Office Action mailed Dec. 3, 2010, 15 pgs.
U.S. Appl. No. 11/146,571, Non Final Office Action mailed Mar. 4, 2009, 13 pgs.
U.S. Appl. No. 11/146,571, Non Final Office Action mailed Jun. 3, 2008, 9 pgs.
U.S. Appl. No. 11/146,571, Non Final Office Action mailed Jun. 28, 2010, 18 pgs.
U.S. Appl. No. 11/146,571, Reply Brief filed Sep. 12, 2011, 14 pgs.
U.S. Appl. No. 11/146,571, Response filed Jan. 22, 2009 to Final Office Action mailed Oct. 14, 2008, 8 pgs.
U.S. Appl. No. 11/146,571, Response filed May 10, 2010 to Final Office Action mailed Nov. 24, 2009, 9 pgs.
U.S. Appl. No. 11/146,571, Response filed Sep. 3, 2008 to Non Final Office Action mailed Jun. 3, 2008, 7 pgs.
U.S. Appl. No. 11/146,571, Response filed Sep. 3, 2009 to Non Final Office Action mailed Mar. 4, 2009, 5 pgs.
U.S. Appl. No. 11/146,571, Response filed Sep. 28, 2010 to Non Final Office Action mailed Jun. 28, 2010, 14 pgs.
U.S. Appl. No. 11/681,268, filed Mar. 2, 2007, 12 pgs.
U.S. Appl. No. 13/027,697, Notice of Allowance mailed Feb. 1, 2012, 11 pgs.
U.S. Appl. No. 13/027,697, Preliminary Amendment filed Feb. 15, 2011, 7 pgs.
"Welding Handbook: Resistance and Solid-State Welding and Other Joining Processes", 7the Edition, vol. 3, (1980), 317-317, 326.
Linnert, "Welding Metallurgy", AWS, 4th Edition, vol. 1, (1994), 591-592.
Pineau, et al., "The Investigation and Production of Titanium-Tantalum Junction Diffusion Bonded at High Temperature (855C to 920C); the Influence of Temperature, Time Pressure and Roughness on the Mechanical Properties, and the Optimisation of the Bonded Conditions", Royal Aerospace Establishment Farnborough, (Jan. 1990), 1 pg.
European Application Serial No. 03253855.5, European Search Report mailed Jan. 21, 2004, 3 pgs.
European Application Serial No. 03253855.5, Office Action mailed Jan. 14, 2011, 3 pgs.
European Application Serial No. 03253855.5, Office Action mailed Jan. 25, 2011, 14 pgs.
European Application Serial No. 03253855.5, Office Action mailed Jan. 26, 2011, 6 pgs.
European Application Serial No. 03253855.5, Office Action mailed May 28, 2004, 4 pgs.
European Application Serial No. 03253855.5, Office Action mailed Jul. 8, 2008, 4 pgs.
European Application Serial No. 03253855.5, Office Action mailed Jul. 21, 2011, 4 pgs.
European Application Serial No. 03253855.5, Office Action mailed Nov. 14, 2006, 4 pgs.
European Application Serial No. 03253855.5, Response filed Jan. 9, 2009 to Office Action mailed Jul. 8, 2008, 8 pgs.
European Application Serial No. 03253855.5, Response filed Jan. 25, 2011 to Office Action mailed Oct. 14, 2010, 6 pgs.
European Application Serial No. 03253855.5, Response filed Apr. 4, 2007 to Office Action mailed Nov. 14, 2006, 12 pgs.
European Application Serial No. 03253855.5, Response filed Sep. 7, 2011 to Office Action mailed Jul. 21, 2011, 4 pgs.
European Application Serial No. 03253855.5, Response filed Oct. 7, 2004 to Office Action mailed May 28, 2004, 30 pgs.
European Application Serial No. 03253855.5, Response filed Dec. 23, 2010 to Summons to Attend Oral Proceedings mailed Oct. 14, 2010, 36 pgs.
European Application Serial No. 03253855.5, Summons to Attend Oral Proceedings mailed Oct. 14, 2010, 6 pgs.

\* cited by examiner

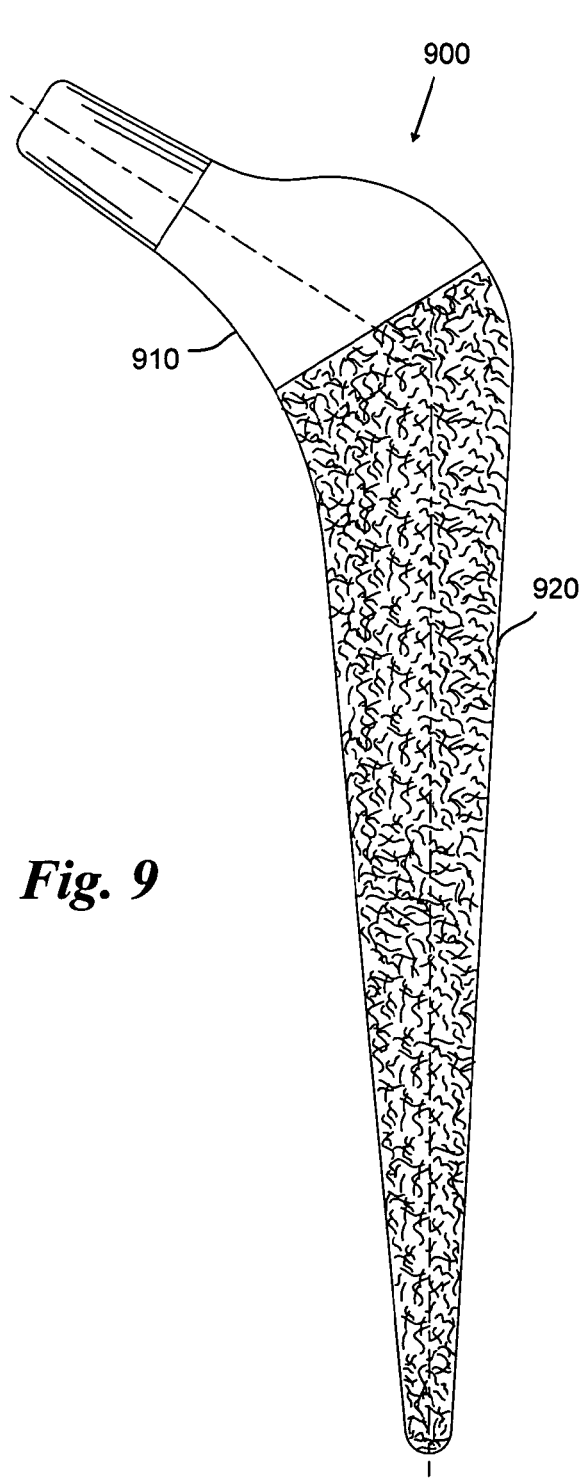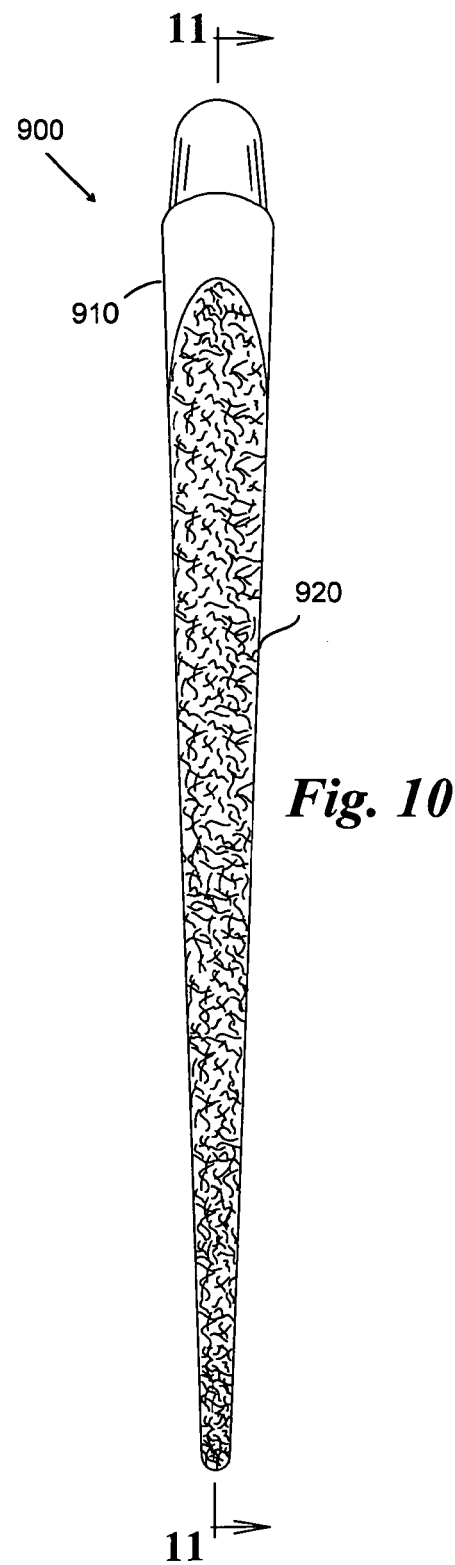
Fig. 9
Fig. 10

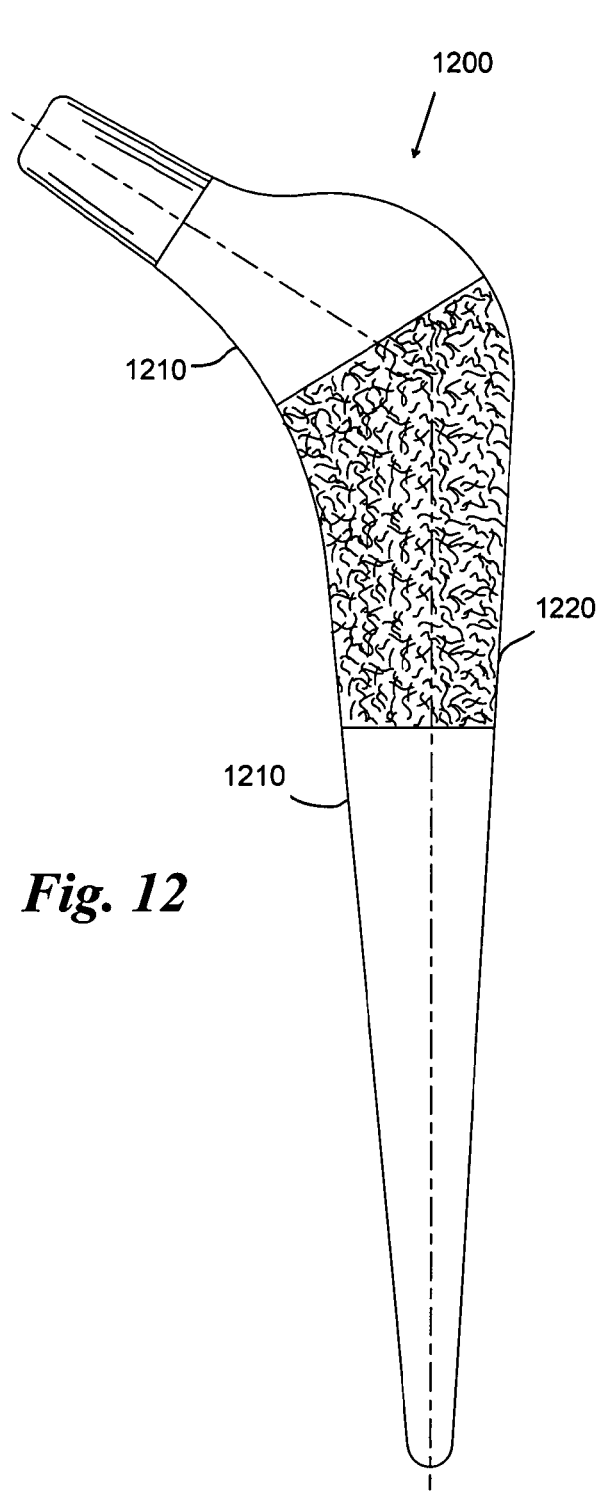
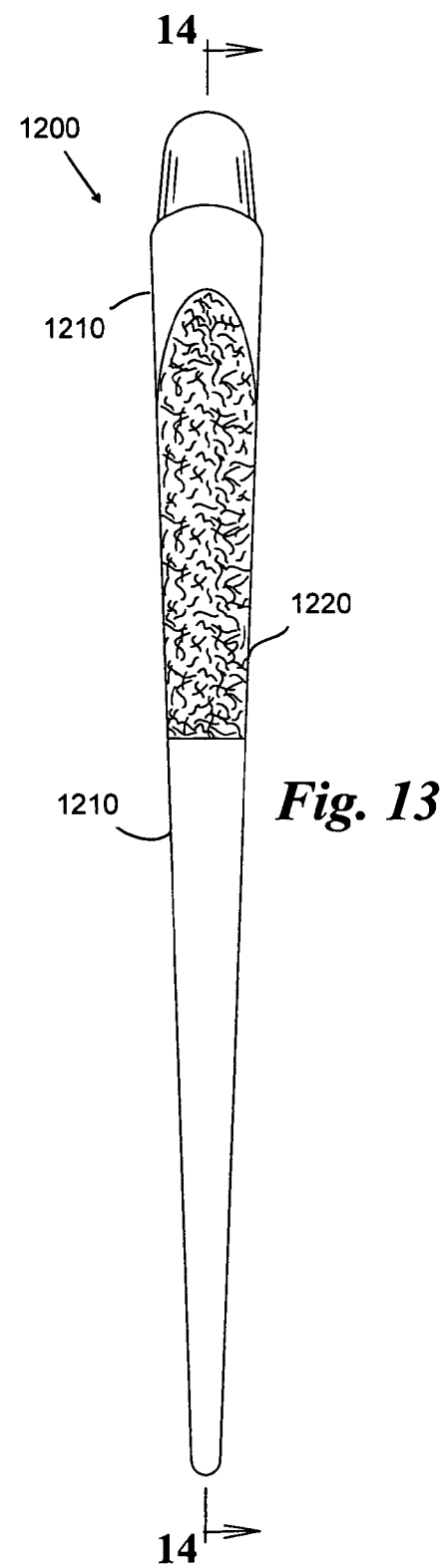
Fig. 12
Fig. 13

METHOD FOR ATTACHING A POROUS METAL LAYER TO A METAL SUBSTRATE

CROSS REFERENCE TO RELATED APPLICATIONS

This application is a divisional of U.S. patent application Ser. No. 13/027,697, filed Feb. 15, 2011, now U.S. Pat. No. 8,191,760, which is a continuation of U.S. patent application Ser. No. 11/109,166 filed Apr. 18, 2005, now U.S. Pat. No. 7,918,382, which is a continuation-in-part of U.S. patent application Ser. No. 10/455,846, filed Jun. 6, 2003, now U.S. Pat. No. 6,945,448, which claims priority to U.S. Provisional Patent Application Ser. No. 60/389,615, filed Jun. 18, 2002, the disclosures of which are hereby explicitly incorporated by reference herein.

FIELD OF THE INVENTION

The present invention relates to orthopedic implants of the type having a porous surface into which bone tissue can grow or bone cement can enter and, more particularly, to a method of bonding a porous metal structure, such as porous titanium or porous tantalum onto a metal substrate preferably comprising a titanium-based or cobalt-based alloy.

BACKGROUND

Orthopedic implant devices commonly include a porous structure of desired thickness, generally 0.5 to 5.0 mm, on the bone contacting surface of the implant to promote bone growth there through and to enhance attachment of the device to adjacent bone tissue. Growth of bone into an implant is advantageous in that the same allows for increased fixation of the implant.

Accordingly, it is desirable to promote as much bone growth into an implant as possible. Various methods have been developed for manufacturing an orthopaedic implant device having a porous surface, including plasma spraying of metal powder, sintering of metal beads, and diffusion bonding of metal wire mesh. See for example, the following patents, the disclosures of which are hereby incorporated by reference and briefly described herein.

U.S. Pat. No. 3,906,550 to Rostoker et al. discloses a porous metal structure adapted for attachment to a prosthesis. The fiber metal is molded into the desired shape using dies. The fiber metal is then sintered together to form metallurgical bonds within the pad and between fiber metal pad and the substrate.

U.S. Pat. No. 3,605,123 to Hahn discloses a metallic bone implant having a porous metallic surface layer. The porous layer may be secured to the implant by a plasma spray method or by other suitable means.

U.S. Pat. No. 4,636,219 to Pratt et al. discloses a prosthesis including a porous surface comprised of a layered metal mesh structure and a process for fabricating the mesh screen structure for bonding to the prosthesis. The mesh may be bonded to a thin substrate which can then be cut or formed and applied to the body of a prosthesis on a flat surface or contoured into specific shapes by forming.

U.S. Pat. No. 4,570,271 to Sump discloses a prosthesis with a porous coating in which the porous coating is preformed directly into the desired shape which corresponds to the pre-selected surface of the prosthesis. The preformed porous coating is then overlaid onto the pre-selected surface, compressed, and heated to adhere the preformed porous coating to the prosthesis.

U.S. Pat. No. 3,855,638 to Pilliar described the bonding process to a prosthetic device having a solid metallic substrate with a porous coating adhered thereto. A slurry of metallic particles was applied to the substrate, dried and then sintered to establish metallurgical bond between particles and the substrate.

U.S. Pat. Nos. 5,198,308 and 5,323,954 entitled "Titanium Porous Surface Bonded to a Cobalt-Based Alloy Substrate in Orthopaedic Implant Device and Method of Bonding Titanium to a Cobalt-Based Alloy Substrate in an Orthopaedic Implant Device" which are assigned to assignee of the present invention teaches diffusion bonding of titanium fiber metal pad porous layer to Co—Cr—Mo alloy implants with the use of a thin titanium and or L-605 alloy foil to increase the bond strength of the coating to the substrate and corrosion resistance of the implant.

U.S. Pat. No. 5,104,410 granted to Chowdhary discloses the method of making a surgical prosthetic device, comprising of a composite structure having a solid metal substrate and a porous coating with multiple sintered layers. The porous coating has an external layer to accept bone ingrowth and the chemical composition of the external layer is same as the intermediate layer between the porous coating and the implant surface. The intermediate layer bonds the external porous layer to the substrate. These layers are applied in a process of multiple sintering where each successive layer is individually sintered to the substrate or the proceeding layer, as applicable. This process provides a porous layer having increased strength of attachment between the substrate and the external porous layer.

Titanium is a known biocompatible metal that is often used in orthopedic applications. Porous titanium or porous titanium alloy can be used on the bone contacting surface of an orthopedic implant to promote bone growth there through. Tantalum is another known biomaterial. Tantalum is known to be particularly adept at promoting bone growth. Implex, Inc. has marketed a structured porous tantalum metal biomaterial, described in U.S. Pat. No. 5,282,861, for orthopedic use under the trade name HEDROCEL®. Zimmer, Inc. presently markets essentially the same material in connection with orthopedic implants under the trade name TRABECULAR METAL™. As used herein, TRABECULAR METAL and HEDROCEL are interchangeable. HEDROCEL is described as being more than 80% porous, and closely resembles human trabecular bone in both physical and mechanical properties. In spite of the value of using a porous layer in orthopedic implants, bonding porous metal to a metal substrate such as cobalt alloy or titanium alloy has been difficult, especially in the case of HEDROCEL. The reason for this difficulty is that metallurgically bonding two components generally requires a large amount of contact between the surfaces at which the bond is desired. The porosity of HEDROCEL results in sparse contact with an opposing metal substrate, thereby making sintering or diffusion bonding difficult. Moreover, this porosity also makes it difficult to maintain the narrow dimensioning tolerances for machined HEDROCEL, components. The binding mixture, therefore, also serves to fill in "gaps" or "spaces" that may exist between a HEDROCEL porous layer of desired shape and a corresponding metal substrate.

Thus, a need exists for a method of bonding a porous metal structure to a metal substrate.

An additional need exists for a method of bonding a porous metal surface to a component of an orthopedic implant device comprising a solid metal, such as cobalt-chrome alloy or titanium alloy.

SUMMARY OF THE INVENTION

The present invention provides a method of bonding a porous metal layer, comprising for example, HEDROCEL, to a titanium alloy or cobalt alloy substrate. More specifically, the bonding process of the present invention involves bonding a porous metal layer directly onto titanium alloy or cobalt alloy surfaces using a sintering or diffusion bonding process that includes a means for producing good surface contact between the porous metal and the substrate.

In one embodiment, the method of the present invention comprises: providing a metal substrate; providing a binding mixture; providing a porous metal structure; applying the mixture to the substrate or to the porous metal; placing the porous metal structure against the substrate such that the binding mixture is disposed between the porous metal and the substrate, thereby forming an assembly; and subjecting the assembly to heat and/or pressure thereby metallurgically bonding the porous metal to the substrate. In this first embodiment, the binding mixture is used to provide contact between the porous metal and the substrate.

In another embodiment, the method of the present invention comprises: providing a metal substrate; providing the porous metal structure; "contouring" the surface of (as defined subsequently herein) of the porous metal structure; placing the porous metal structure against the substrate, thereby forming an assembly; and subjecting the structure to heat and/or pressure to metallurgically bond the porous metal structure to the substrate. In this second embodiment, surface contact between the porous metal structure and the substrate is achieved by contouring the surface of the porous metal prior to placing it against the substrate.

In another embodiment, the method of the present invention comprises: providing a solid metal substrate; providing a porous metal structure; contouring a surface of the porous metal structure; placing the porous structure against the substrate such that the contoured surface of the porous metal structure is disposed against the substrate, thereby forming an assembly; applying heat and pressure to the assembly in conjunction with thermal expansion of the substrate in order to metallurgically bond the porous structure and the substrate; and removing mass from the substrate after the porous structure is bonded to the substrate, thereby finish processing the assembly.

The invention, in another form thereof, further provides a method of making an orthopedic implant having a porous metal layer bonded to a metal component of an implant.

An advantage of the bonding method of the present invention is that a porous metal structure can be bonded to titanium-based and cobalt-based alloy substrates.

A further advantage of the bonding method of the present invention is that a single bonding process is employed thereby protecting the metallurgical properties of the component alloys of the assembly.

Another advantage of the present invention is that orthopaedic implant devices produced according to the present invention comprise a porous metal surface provided on titanium-based and cobalt-based alloy substrates with enhanced bond strength and corrosion resistance.

Other advantages of the present invention will be apparent to those of skill in the art upon reviewing the appended specification, drawings, and claims.

The above-noted features and advantages of the present invention, as well as additional features and advantages, will be readily apparent to those skilled in the art upon reference to the following detailed description and the accompanying drawings, which include a disclosure of the best mode of making and using the invention presently contemplated.

BRIEF DESCRIPTION OF THE DRAWINGS

FIG. 9 is a first plan view of a femoral hip component of an endoprosthetic hip joint constructed according to the method of FIG. 8;

FIG. 10 is a second plan view of the femoral hip component of FIG. 9;

FIG. 12 is a first plan view of an alternative femoral hip component of an alternative endoprosthetic hip joint constructed according to the method of FIG. 8;

FIG. 13 is a second plan view of the alternative femoral hip component of FIG. 12.

DETAILED DESCRIPTION OF EXEMPLARY EMBODIMENTS)

Figure 1:
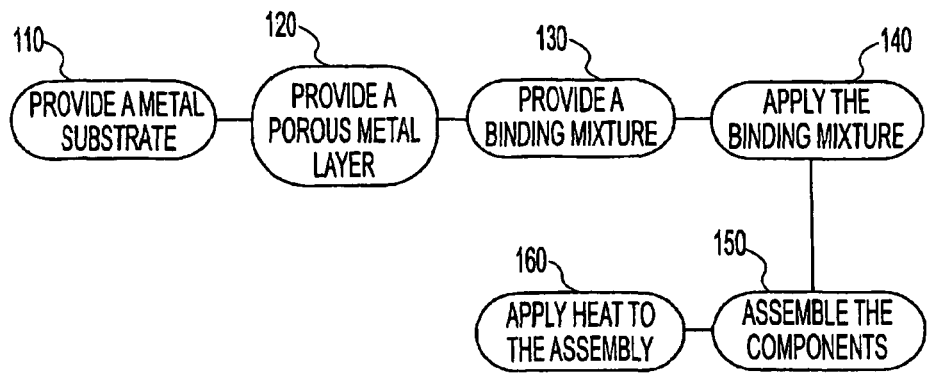
FIG. 1 is a diagrammatic view of a first embodiment of the present invention.

Like reference numerals refer to like parts throughout the following description and the accompanying drawings.

Figure 4:
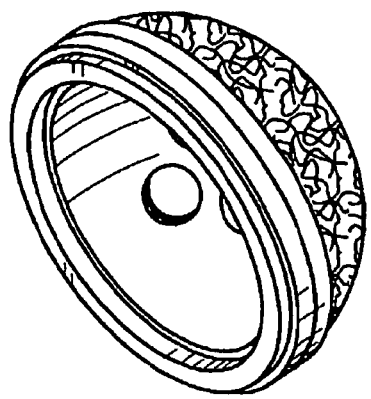
FIG. 4 is a perspective view of an acetabular cup assembly constructed according to the present invention.
Figure 5:
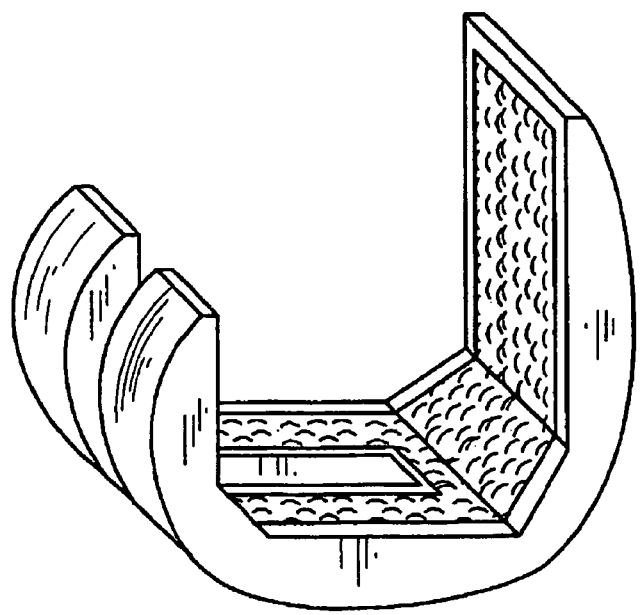
FIG. 5 is a perspective view of the femoral component of an endoprosthetic knee joint constructed according to the present invention.

Referring now to FIG. 1, there is shown a diagrammatic view of a first embodiment of the present invention. Generally, Block 110 represents providing a metal substrate. In the present invention, the term "metal substrate" refers to titanium based or cobalt based alloys as are often used in orthopedic applications. Titanium alloys such as Ti-6Al-4V alloy, Ti-6Al-7Nb alloy, Ti15Mo alloy, or commercially pure titanium (having a rating of ASTM F-67, F-136, F-620, F-1108, F-1295, F-1341, F-1472, F-1713, F-1813, or F-2066) are preferred. Cobalt based alloys, specifically cast Co—Cr—Mo alloy or wrought Co—Cr—Mo alloy, having an ASTM designation of F-75 or F-1537 respectively, may also be used. In some instances, it is desirable to use a cobalt based alloy having a layer of commercially pure titanium or titanium alloy plasma sprayed thereon. The above stated metals are preferred because of their strength, corrosion resistance and compatibility. In the orthopedic applications for which the method of the present invention may most commonly, although not exclusively, be used, the metal substrate may be shaped in a manner desirable to function as a component of an orthopedic implant, for example, an acetabular cup assembly as shown in FIG. 4 of the present invention or a femoral component for an endoprosthetic knee as shown in FIG. 5 of the present invention. However, those skilled in the art will appreciate that the present invention is applicable to any application wherein one desires to metallurgically bond a porous metal layer to a metal substrate.

Referring still to FIG. 1, there is shown Block 120 which represents providing a porous metal layer. In a preferred embodiment, a porous tantalum structure is used. The porous metal layer is preferably provided in a desired shape suitable for a particular application. For example, a hemispherical shape may be used as a shell for an acetabular cup of an orthopedic implant. The porous metal layer may also be provided as a pad for use on the bone contacting surface of a standard femoral component for an orthopedic knee implant.

In order to provide a strong metallurgical bond (i.e. a pull apart strength of at or above about 2900 p.s.i.) between the metal substrate and porous metal layer via sintering or diffusion bonding, there must be sufficient surface contact between the components. Those skilled in the art will appreciate that, on a microscopic level, neither the surface of the metal substrate, nor the surface of the porous metal layer is perfectly contoured. Thus, a less than critical amount of surface contact for producing a metallurgical bond will exist between a porous metal layer and a metal substrate disposed directly against one another, unless a means of producing sufficient surface contact is provided. In addition, the fact that narrow tolerance ranges are difficult to obtain for machined shapes comprising porous metal structures, such as HEDROCEL, makes it likely that one will find gaps between the adjacent surfaces of a porous layer placed against a metal substrate.

One preferred means of ensuring that sufficient surface contact is present is to provide a binding mixture between the substrate and porous layer. The binding mixture fills in the porous surface of the porous tantalum layer thereby "contouring" the surface, and it fills in the "gaps" between the porous layer and the substrate, thereby providing sufficient surface contact for metallurgically bonding the porous tantalum layer and the metal substrate.

Thus, referring again to FIG. 1, there is shown a Block 130 which represents providing a binding mixture. Generally, the binding mixture of the present invention comprises an organic binder with sufficient adhesive strength to hold a metal powder in place. It is preferable to choose an organic binder that decomposes within the temperate range of the diffusion bonding or sintering step discussed subsequently herein. The organic binder may be selected from the group consisting of gelatin, glycerin, polyvinyl alcohol ("PVA") or a combination of the same. The binding mixture further comprises powdered metal wherein the metal is preferably the same as the metal used to form the metal substrate. However, different metals that have good mutual solubility between the substrate and the material comprising the porous layer may be used in the binding mixture. For example, cobalt-chrome alloy, hafnium, manganese, niobium, palladium, titanium-6, aluminum-4, vanadium alloy, aluminum-7, titanium-nickel alloy, zirconium, zirconium alloys, Ti-6Al-4V, Ti-6Al-7Nb, commercially pure titanium, titanium alloys, and cobalt-chromium-molybdenum.

The binding mixture preferably comprises about 68% by volume powdered metal and about 32% by volume of a solution comprising 10% PVA and 90% water. However the binding mixture may comprise between above about 10% by volume powdered metal and about 95% by volume powdered metal. Exemplary binding mixture configurations are shown in the EXAMPLES section of this application.

Referring still to FIG. 1 there is shown in Block 140, representing the step of applying the binding mixture to the porous layer. In the preferred embodiment, the binding mixture is applied to the porous layer, and for clarity of explanation, the present invention is described as having the binding mixture applied to the porous layer. However, it is to be appreciated that the binding mixture can also be applied to the substrate, depending on the shape of the components that one desires to bond and the viscosity of a chosen binding mixture.

In any event, it is desirable to apply the binding mixture as evenly as possible. Preferably, the binding mixture is sprayed onto the porous layer, but the porous layer may also be dipped into the binding mixture, or the binding mixture may be painted on porous layer. Alternatively, the same techniques may be used to apply the binding mixture to the substrate. An example of a technique for applying a binding mixture is illustrated in U.S. Pat. No. 5,198,308, assigned to the assignee of the present application, and whose subject matter is hereby incorporated by reference into the present application.

Referring again to FIG. 1, there is shown Block 150, which represents the step of assembling the substrate and the porous metal layer such that the binding mixture is disposed therebetween. This step may be accomplished by any desirable means known in the art whereby a first component is placed against a second component.

Referring again to FIG. 1 there is shown in Block 160, which represents the step of heating the assembly, to complete the bonding process. In a preferred embodiment, the heating step comprises: heating the assembly in a debinding cycle to a temperature of within about 100° C. to about 600° C. preferably in an inert atmosphere consisting essentially of argon or helium having at most trace amounts of oxygen or nitrogen. Alternatively, the heating step may be conducted in a partial vacuum environment having a pressure of 0.01 torr or less. The assembly is held at this temperature for about 1 hour to about 4 hours to remove the organic binder contained in the binding mixture. A sintering cycle is then run at about 800° C. to 1600° C. for about 1 to 4 hours.

Figure 2:
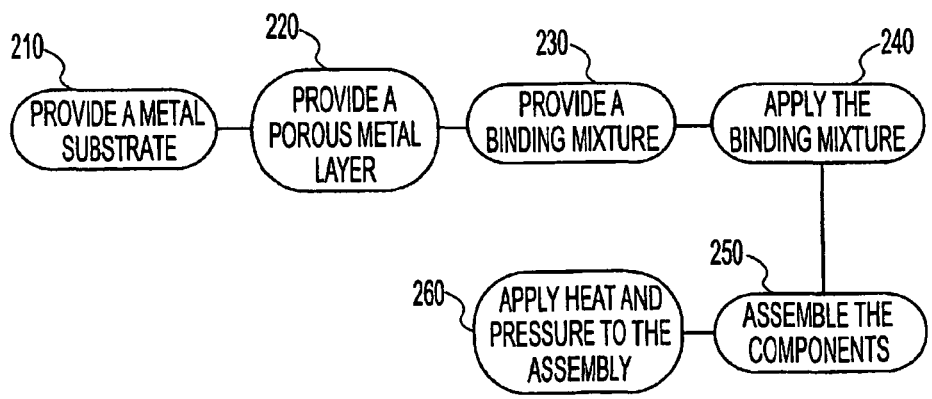
FIG. 2 is a diagrammatic view of a second embodiment of the present invention.

Referring now to FIG. 2, there is shown an alternative embodiment of the present invention, comprising the steps of providing a metal substrate, Block 210; providing a porous tantalum layer, Block 220; providing a binding mixture, Block 230; applying the binding mixture to the substrate, Block 240; assembling the parts, Block 250; and applying heat and pressure to the assembly, Block 260.

In the alternative embodiment shown in FIG. 2, the steps are largely as described above; however, the step of applying heat and pressure, shown in Block 260, comprises: heating the assembly to within a temperature of within about 100° C. to about 600° C., preferably in an inert or partial vacuum environment, and under a clamping pressure of between 200 and 1200 p.s.i. The clamping pressure is useful in assuring suitable surface contact between the substrate and porous layer. Also, the heating temperature required to achieve a particular bond strength between the porous component and substrate is generally inversely proportional to the amount of clamping pressure used. The assembly is held at the desired temperature and pressure for about 1 hour to about 4 hours.

Figure 3:
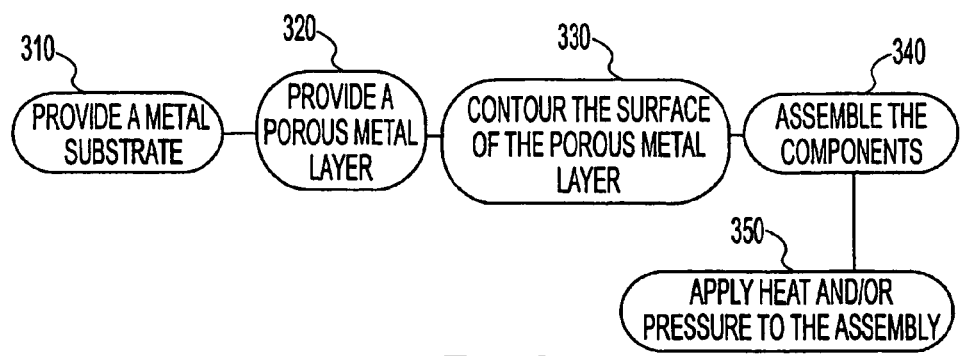
FIG. 3 is a diagrammatic view of a third embodiment of the present invention.

In FIG. 3, there is shown another embodiment of the present invention comprising the steps of: providing a metal substrate, Block 310; providing a porous tantalum layer, Block 320; contouring the surface of the porous metal layer, Block 330; assembling the parts, Block 340; and applying heat and/or pressure to the assembly, Block 350.

In the embodiment of FIG. 3, the steps of providing a metal substrate, Block 310 and providing a tantalum porous layer, Block 320 are the same as described previously herein with regard to the embodiment of FIG. 1. However, in this third embodiment of the present invention, no binding mixture is used to enable the porous tantalum layer to have adequate surface contact with the substrate. Instead, an alternative means is used to contour the porous tantalum layer to ensure that sufficient surface contact exists between the components of the assembly. Specifically, as represented by Block 330, the surface of the porous layer is mechanically contoured or smeared to provide more surface contact with the substrate.

Generally, machining methods well known in the art are used to contour the surface of the porous tantalum layer a desirable amount. Alternatively, electro discharge machining may be used to contour the surface of the porous tantalum layer.

Referring still to FIG. 3, the substrate and porous layer are assembled as shown in Block 340, and heat and/or pressure are applied to the assembly as shown in Block 350. The step of Block 350 comprises: heating the assembly to within a temperature of within about 800° C. to about 1600° C. in a low oxygen or partial vacuum environment. A clamping pressure may be used if desired. The assembly is held at this temperature and pressure for about 1 hour to about 4 hours.

Figure 6:
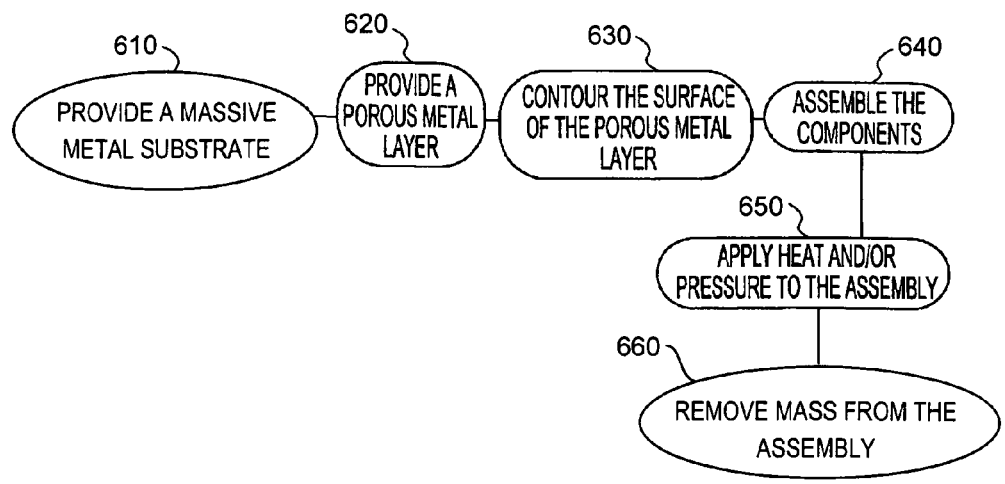
FIG. 6 is a diagrammatic view of a fourth embodiment of the present invention.

In FIG. 6, there is shown another embodiment of the present invention comprising the steps of: providing a massive solid metal substrate, Block 610; providing a porous metal layer, Block 620; contouring the surface of the porous metal layer, Block 630; assembling the parts, Block 640; applying heat and pressure to the assembly, Block 650; and removing mass from the substrate, Block 660.

In the embodiment of FIG. 6, the step of providing a metal substrate, Block 610 is the same as the corresponding step described previously herein with regard to the embodiment of FIG. 3, with the exception that initially the substrate is significantly more massive such that it will exhibit a greater thermal expansion when heated. For example, an unfinished acetabular cup substrate in the form of a solid (not hollowed) hemisphere or any other suitably massive substrate may be used.

Block 620 is the same as described previously herein with regard to the embodiment of FIG. 3. In this fourth embodiment, no binding mixture is used to enable the porous tantalum layer to have adequate surface contact with the substrate. As represented by Block 630, the surface of the porous layer is mechanically contoured or smeared to provide more surface contact with the substrate. Alternatively, electro discharge machining may be used to contour the surface of the porous tantalum layer.

Referring still to FIG. 6, the substrate and porous layer are assembled as indicated by Block 640, and heat and pressure are applied to the assembly as indicated by Block 650. The step of Block 650 comprises: heating the assembly to within a temperature of within about 800° C. to about 1600° C. in a low oxygen or partial vacuum environment, with a clamping pressure of about 400-500 p.s.i. The assembly is held at this temperature and pressure for about 1 hour to about 4 hours. It is noted that the increased thermal expansion works in conjunction with the clamping pressure to effectively increase the surface contact between the substrate and the porous layer as they are heated, thus contributing to the effectiveness of the bonding process.

Figure 7:
FIG. 7 is a perspective view of an unfinished acetabular cup assembly constructed according to the present invention.

Finally, as indicated by Block 660, after the porous layer is bonded to the substrate the assembly is finished by machining away the excess mass from the substrate to form it into the desired final shape. For example, an initially unfinished acetabular cup assembly (e.g., including a solid, not hollowed, massive hemispherical substrate) such as the one shown in FIG. 7 may be suitably hollowed into a finished acetabular cup assembly such as the one shown in FIG. 4.

Figure 8:
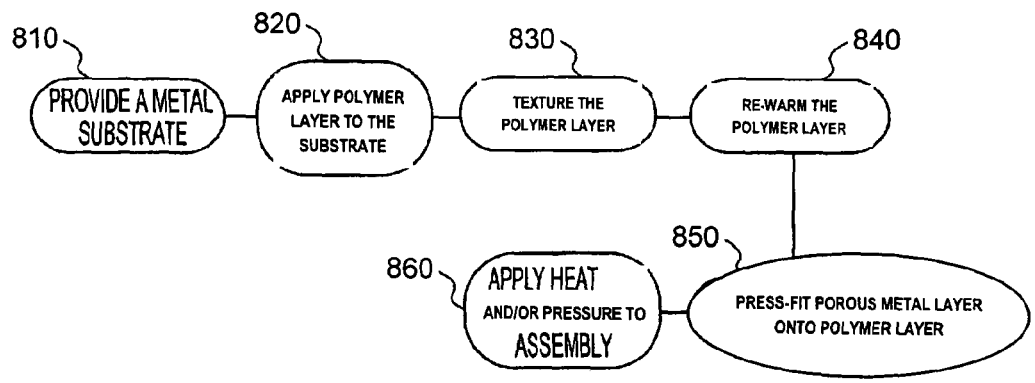
FIG. 8 is a diagrammatic view of a fifth embodiment of the present invention.

In FIG. 8, there is shown another embodiment of the present invention comprising the steps of: providing a metal substrate in a like manner to any of the corresponding step(s) described previously herein with regard to any of the foregoing alternative embodiments, Block 810; injection molding or otherwise applying a thin layer of high strength polymer from the polyaryl ether ketone family (e.g., polyaryl ether ketone ("PEAK"), ultra polyaryl ether ketone ("Ultra PEAK"), or the like) or any other suitable polymer to the surface of the substrate, Block 820; texturing the polymer layer by molding, machining, or otherwise forming small spikes, posts, ratchet ramps, or the like in the surface of the polymer layer, Block 830; re-warming or re-heating the polymer layer (by conduction, convection, application of ultrasonic energy, or any other suitable means) to somewhat soften (but not dissociate) the polymer layer, Block 840; press-fitting a porous metal layer onto the softened polymer layer, Block 850; and applying suitable heat and/or pressure to the assembly to enhance interdigitation of the polymer layer into the porous metal layer, Block 860.

It is noted that in the embodiment of FIG. 8, the texturing in Block 830 provides features in the surface of the polymer layer that help restrain the porous metal layer from slipping or otherwise moving on the polymer layer. However, it is also noted that Block 830 may be omitted in alternative embodiments. Further, while in the embodiment of FIG. 8 the re-warming of the polymer layer in Block 840 softens the polymer layer to facilitate press-fitting the porous metal layer onto the softened polymer layer in Block 850, it is noted that Block 840 may be omitted in alternative embodiments.

Additionally, it should be appreciated that in the embodiment of FIG. 8 and corresponding alternative embodiments friction between the polymer layer and the porous metal layer helps restrain dissociation of the porous metal layer from the assembly. Meanwhile, the interposition of the polymer layer between the substrate and the porous metal layer also help prevent formation of metallic debris. Furthermore, it is believed that the embodiment of FIG. 8 and corresponding alternative embodiments may avoid compromises in fatigue strength exhibited by historical methods for attaching porous metal layers to substrates.

FIG. 9 is a first plan view of a femoral hip component 900 of an endoprosthetic hip joint constructed according to the method of FIG. 8. As at least partially discernable in FIG. 9, femoral hip component 900 includes a metal substrate 910 and a porous metal layer 920.

FIG. 10 is a second plan view of the femoral hip component 900. Metal substrate 910 and porous metal layer 920 are both at lease partially discernable in FIG. 10.

Figure 11:
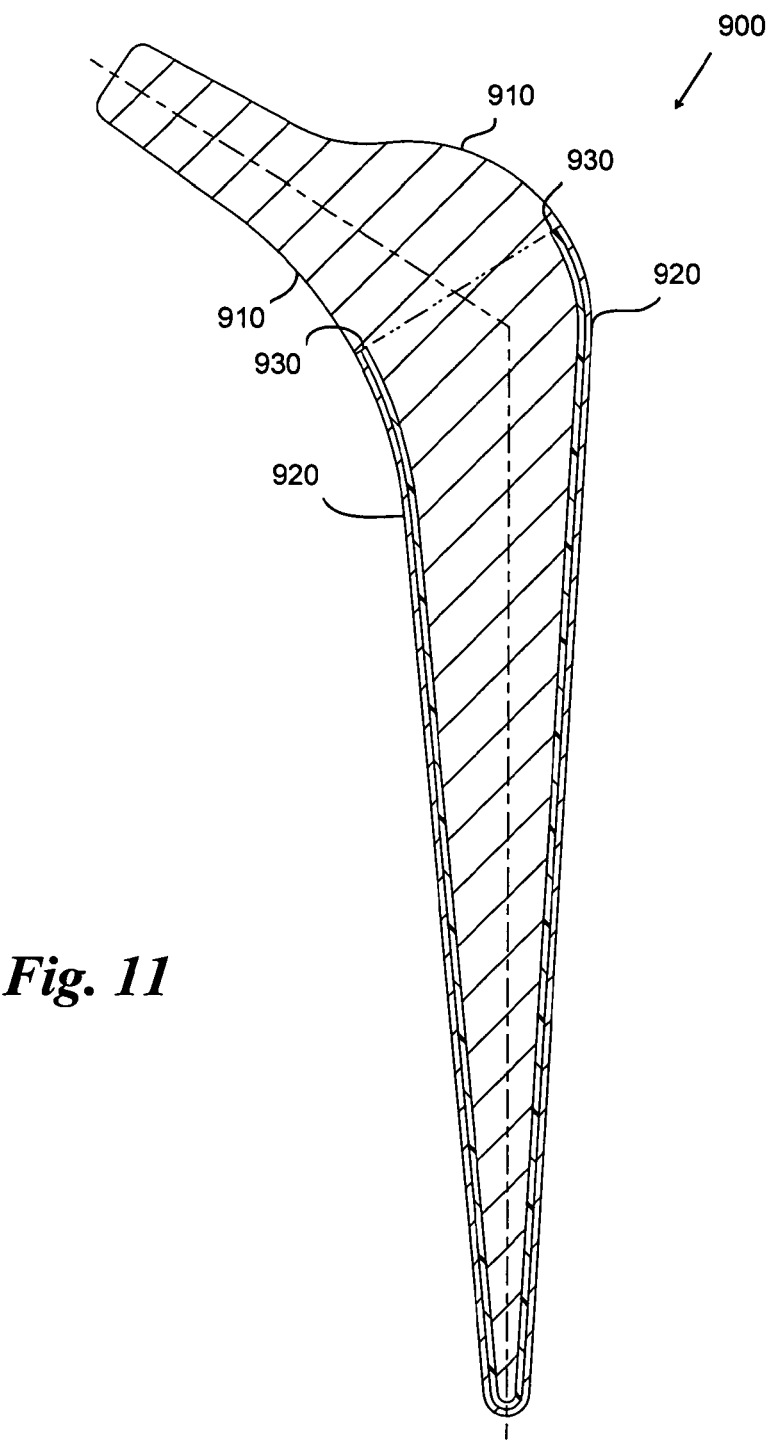
FIG. 11 is a cross-sectional view of the femoral hip component of FIG. 9 and FIG. 10 taken along line 11-11 of FIG. 10.

FIG. 11 is a cross-sectional view of the femoral hip component 900 taken along line 11-11 of FIG. 10. Metal substrate 910 and porous metal layer 920 are at lease partially discernable in FIG. 11. Additionally, as at least partially discernable in FIG. 11, femoral hip component 900 further includes a polymer layer 930 interposed between metal substrate 910 and porous metal layer 920.

FIG. 12 is a first plan view of an alternative femoral hip component 1200 of an alternative endoprosthetic hip joint constructed according to the method of FIG. 8. As at least partially discernable in FIG. 12, femoral hip component 1200 includes a metal substrate 1210 and a porous metal layer 1220.

FIG. 13 is a second plan view of the alternative femoral hip component 1200. Metal substrate 1210 and porous metal layer 1220 are both at lease partially discernable in FIG. 13.

Figure 14:
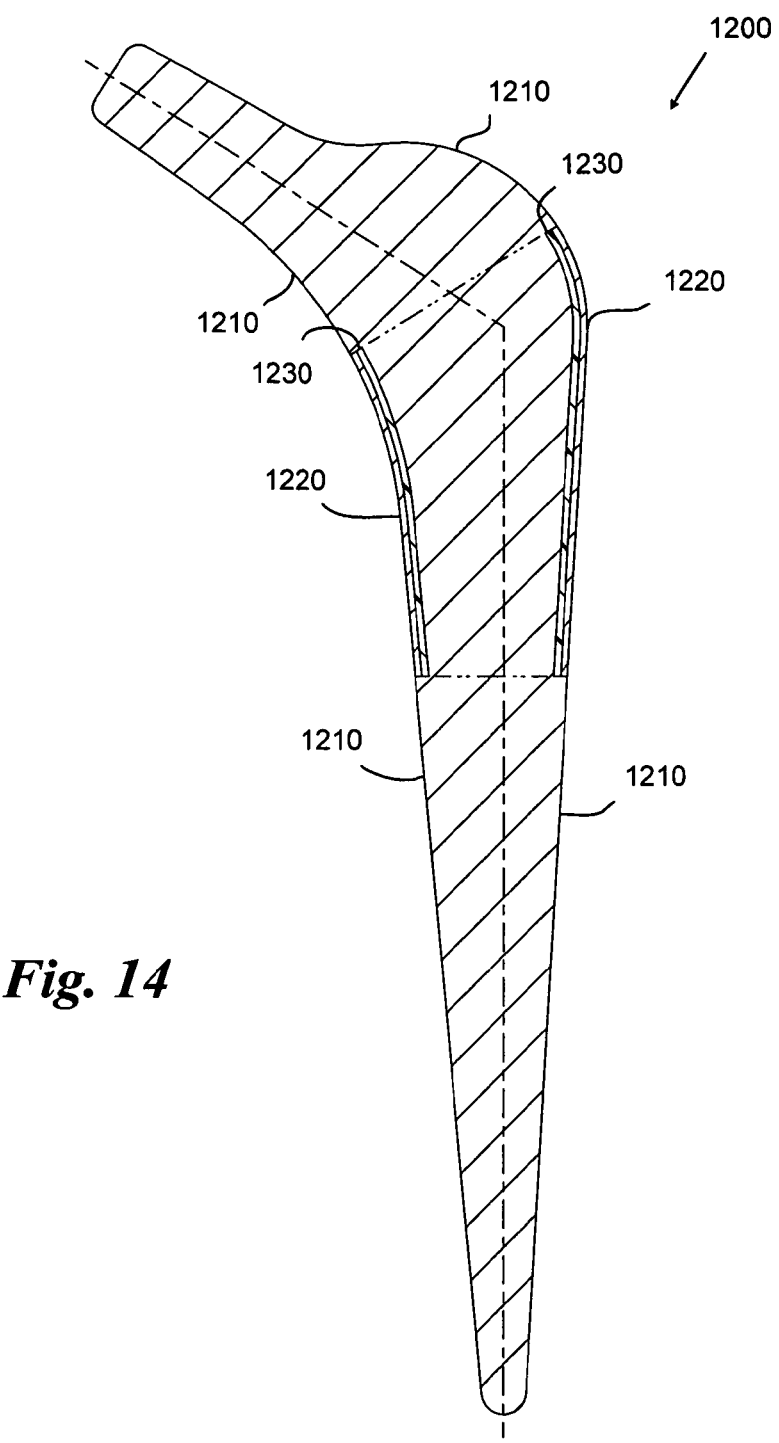
FIG. 14 is a cross-sectional view of the alternative femoral hip component of FIG. 12 and FIG. 13 taken along line 14-14 of FIG. 13.

FIG. 14 is a cross-sectional view of the alternative femoral hip component 1200 taken along line 14-14 of FIG. 13. Metal substrate 1210 and porous metal layer 1220 are at lease partially discernable in FIG. 14. Additionally, as at least partially discernable in FIG. 14, femoral hip component 1200 further includes a polymer layer 1230 interposed between metal substrate 1210 and porous metal layer 1220.

Those skilled in the art will appreciate that for each embodiment of the invention the times, temperatures, and pressures may be manipulated to vary the bond strength between the porous layer and the substrate and to vary the effects of the process on the mechanical properties of the porous layer and the substrate. In addition, the multiple cycles of applying heat and/or pressure may used to similarly affect the strength of bond between components or the mechanical properties of the substrate or porous layer.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

EXAMPLES

| SUBSTRATE MATERIAL | POROUS LAYER | CYCLE TEMPERATURE | CYCLE TIME | ENVIRONMENT | CLAMPING PRESSURE | BINDING MIXTURE |
|---|---|---|---|---|---|---|
| Ti—6AL—V | HEDROCEL | 955° C. | 2 cycles at 4 hours each | Argon | 400 p.s.i. | 68% powdered metal + 32%(10% PVA, 90% water solution) |
| Ti—6AL—V | HEDROCEL | 955° C. | 2 cycles at 4 hours each | Helium | 400 p.s.i. | 68% powdered metal + 32%(10% PVA, 90% water solution) |
| Ti—6AL—V | HEDROCEL | 955° C. | 2 cycles at 4 hours each | Argon | 400 p.s.i. | N/A |
| Ti—6AL—V | Machined HEDROCEL | 350° C. (debind) + 1200° C. (sintering) | 3 hours (debind) + 4 hours (sintering) | 0.01 Torr | N/A | 68% powdered metal + 32%(10% PVA, 90% water solution) |
| Co—Cr—Mo | Machined HEDROCEL | 1094° C. | 2 cycles at 4 hours each | 0.01 Torr | 400 p.s.i. | 68% powdered metal + 32%(10% PVA, 90% water solution) |

What is claimed is:

1. A method for attaching a porous metal layer to a metal substrate of an orthopedic implant, the method comprising the steps of:
   providing the metal substrate;
   injecting a polymer that is heated onto the metal substrate in a mold so as to form an injection-molded polymer layer on the metal substrate, the injection-molded polymer layer including an outer surface shaped by the mold;
   after the applying step, re-heating the injection-molded polymer layer on the metal substrate to form a softened polymer layer on the metal substrate; and
   press-fitting the porous metal layer onto the softened polymer layer to form an assembly.

2. The method of claim 1, further comprising the step of texturing an outer surface of the polymer layer before the re-heating step, wherein the press-fitting step comprises press-fitting the porous metal layer onto the textured outer surface of the polymer layer.

3. The method of claim 2, wherein the texturing step comprises molding or machining the outer surface of the polymer layer.

4. The method of claim 2, wherein the texturing step comprises forming a plurality of spikes, posts, or ratchet ramps in the outer surface of the polymer layer.

5. The method of claim 1, wherein the injection-molded polymer layer includes a textured outer surface shaped by the mold.

6. The method of claim 1, wherein the metal substrate exhibits a hemispherical shape.

7. The method of claim 1, wherein the re-heating step softens the injection-molded polymer layer without disassociating the injection-molded polymer layer.

8. The method of claim 6, wherein the porous metal layer is a pre-shaped porous metal structure exhibiting a hemispherical shape.

9. The method of claim 1, further comprising the step of applying at least one of heat and pressure to the assembly during the press-fitting step to enhance interdigitation of the softened polymer layer into the porous metal layer.

10. A method for attaching a porous metal layer to an outer surface of a hemispherical metal substrate of an orthopedic implant, the method comprising the steps of:
    providing the hemispherical metal substrate;
    injecting a polymer that is heated onto the outer surface of the hemispherical metal substrate in a mold so as to form an injection-molded hemispherical polymer layer on the outer surface of the hemispherical metal substrate, the injection-molded hemispherical polymer layer including a textured outer surface shaped by the mold;
    re-heating the injection-molded hemispherical polymer layer on the hemispherical metal substrate to soften the textured outer surface of the hemispherical polymer layer;
    providing a pre-shaped porous metal structure exhibiting a hemispherical shape; and
    press-fitting the pre-shaped porous metal structure exhibiting a hemispherical shape onto the textured and softened outer surface of the hemispherical polymer layer to form an assembly.

11. The method of claim 10, wherein the pre-shaped porous metal structure exhibiting a hemispherical shape consists essentially of porous titanium or porous tantalum.

12. The method of claim 11, wherein the pre-shaped porous metal structure exhibiting a hemispherical shape consists essentially of porous tantalum.

13. The method of claim 11, wherein the pre-shaped porous metal structure exhibiting a hemispherical shape consists essentially of porous titanium.

14. The method of claim 10, further comprising the step of applying at least one of heat and pressure to the assembly to enhance interdigitation of the softened polymer layer into the porous metal structure.

15. The method of claim 10, wherein the textured outer surface includes a plurality of spikes, posts, or ratchet ramps.

16. The method of claim 10, wherein the textured outer surface includes a plurality of spikes.

* * * * *